(12) United States Patent
Nielsen et al.

(10) Patent No.: US 11,911,310 B2
(45) Date of Patent: *Feb. 27, 2024

(54) ADHESIVE WAFER WITH A NEUTRALIZER MATRIX

(71) Applicant: Coloplast A/S, Humlebaek (DK)

(72) Inventors: Lene Feldskov Nielsen, Koebenhavn (DK); Monica Ramos Gallego, Koebenhavn (DK)

(73) Assignee: Coloplast A/S, Humlebaek (DK)

( * ) Notice: Subject to any disclaimer, the term of this patent is extended or adjusted under 35 U.S.C. 154(b) by 431 days.

This patent is subject to a terminal disclaimer.

(21) Appl. No.: 16/761,815

(22) PCT Filed: Nov. 2, 2018

(86) PCT No.: PCT/DK2018/050280
§ 371 (c)(1),
(2) Date: May 6, 2020

(87) PCT Pub. No.: WO2019/091528
PCT Pub. Date: May 16, 2019

(65) Prior Publication Data
US 2021/0177641 A1   Jun. 17, 2021

(30) Foreign Application Priority Data

Nov. 8, 2017   (DK) ................................. 2017 70837

(51) Int. Cl.
*A61F 5/443*   (2006.01)
*C09J 7/40*   (2018.01)
(Continued)

(52) U.S. Cl.
CPC .............. *A61F 5/443* (2013.01); *A61F 5/448* (2013.01); *A61F 13/0259* (2013.01); *C09J 5/08* (2013.01);
(Continued)

(58) Field of Classification Search
CPC ...... A61F 5/443; A61F 5/448; A61F 13/0259; C09J 5/08; C09J 7/401; C09J 11/04; C09J 105/00; C09J 2405/00
See application file for complete search history.

(56) References Cited

U.S. PATENT DOCUMENTS 3,077,192 A   2/1963   Berger
3,302,647 A   2/1967   Marsan
(Continued)

FOREIGN PATENT DOCUMENTS

CN   1226178 A   8/1999
CN   101001650 A1   7/2007
(Continued)

*Primary Examiner* — Scott R. Walshon
(74) *Attorney, Agent, or Firm* — Coloplast Corp., Coloplast A/S; Nick Baumann

(57) ABSTRACT

An adhesive wafer for an ostomy device, the wafer comprising a skin-facing adhesive layer, a backing layer on the non-skin-facing side of the adhesive layer, and a hole for accommodating a stoma. On the central portion of the backing layer is located a release layer being configured to release a neutralizer. The neutralizer is capable of neutralizing or at least minimizing the level of skin or adhesive aggressiveness of the output.

19 Claims, 5 Drawing Sheets

(51) Int. Cl.
*A61F 5/448* (2006.01)
*A61F 13/02* (2006.01)
*C09J 5/08* (2006.01)
*C09J 11/04* (2006.01)
*C09J 105/00* (2006.01)

(52) U.S. Cl.
CPC ............... *C09J 7/401* (2018.01); *C09J 11/04* (2013.01); *C09J 105/00* (2013.01)

(56) References Cited

U.S. PATENT DOCUMENTS

| | | | |
|---|---|---|---|
| 3,522,808 | A | 8/1970 | Worcester |
| 4,121,589 | A | 10/1978 | Mcdonnell |
| 4,265,244 | A * | 5/1981 | Hill .................... A61F 5/445 623/23.64 |
| 4,723,952 | A | 2/1988 | Esposito |
| 5,942,186 | A | 8/1999 | Sanada et al. |
| 6,740,067 | B2 | 5/2004 | Leise, Jr. et al. |
| 7,858,836 | B2 | 12/2010 | Sambasivam |
| 8,652,825 | B2 | 2/2014 | Eiteman et al. |
| 9,084,696 | B2 | 7/2015 | Luce |
| 10,744,224 | B2 | 8/2020 | Israelson et al. |
| 11,278,640 | B2 * | 3/2022 | Stroebech ............ A61L 24/0015 |
| 11,491,043 | B2 | 11/2022 | Langhorn et al. |
| 11,491,254 | B2 | 11/2022 | Olsen et al. |
| 11,612,512 | B2 | 3/2023 | Hansen et al. |
| 2003/0004477 | A1 | 1/2003 | Nielsen et al. |
| 2003/0206944 | A1 | 11/2003 | Cohen et al. |
| 2004/0028708 | A1 * | 2/2004 | Brooks .................. A61K 8/922 424/642 |
| 2006/0036223 | A1 | 2/2006 | Baldwin et al. |
| 2008/0063695 | A1 | 3/2008 | Vitaris |
| 2008/0195016 | A1 | 8/2008 | Bottini |
| 2008/0294129 | A1 | 11/2008 | Giori et al. |
| 2008/0319368 | A1 | 12/2008 | Lykke et al. |
| 2009/0010998 | A1 | 1/2009 | Marchitto et al. |
| 2010/0114044 | A1 | 5/2010 | Cramer et al. |
| 2010/0114045 | A1 | 5/2010 | Cramer et al. |
| 2010/0204664 | A1 | 8/2010 | Bach et al. |
| 2012/0041404 | A1 | 2/2012 | Bach et al. |
| 2012/0282321 | A1 | 11/2012 | Cohen et al. |
| 2012/0302981 | A1 * | 11/2012 | Lam ........................ A61F 5/445 604/338 |
| 2012/0323193 | A1 | 12/2012 | Johannison et al. |
| 2013/0226063 | A1 | 8/2013 | Taylor et al. |
| 2013/0304008 | A1 | 11/2013 | Hanuka et al. |
| 2014/0163495 | A1 | 6/2014 | Nassopoulos |
| 2016/0136323 | A1 | 5/2016 | Leise, III |
| 2018/0008451 | A1 | 1/2018 | Stroebech |
| 2018/0243466 | A1 | 8/2018 | Israelson et al. |
| 2019/0134256 | A1 | 5/2019 | Stroebech |
| 2020/0015996 | A1 * | 1/2020 | Schertiger .............. A61F 5/445 |
| 2020/0046541 | A1 | 2/2020 | Sund et al. |
| 2020/0246177 | A1 | 8/2020 | Hansen et al. |
| 2020/0338230 | A1 | 10/2020 | Israelson et al. |
| 2021/0059912 | A1 | 3/2021 | Gallego et al. |
| 2021/0085510 | A1 | 3/2021 | Langhorn et al. |
| 2021/0113362 | A1 | 4/2021 | Windeballe et al. |
| 2021/0187155 | A1 | 6/2021 | Olsen et al. |
| 2021/0275341 | A1 * | 9/2021 | Hansen ................... A61L 15/56 |
| 2021/0275342 | A1 | 9/2021 | Sund et al. |

FOREIGN PATENT DOCUMENTS

| | | |
|---|---|---|
| CN | 101163585 A | 4/2008 |
| CN | 101279102 A | 10/2008 |
| CN | 102413797 A | 4/2012 |
| CN | 107249519 A1 | 10/2017 |
| EP | 0686381 A1 | 12/1995 |
| EP | 1666008 A2 | 7/2006 |
| EP | 1736136 A1 | 12/2006 |
| EP | 1140009 B2 | 8/2010 |
| EP | 2527823 A1 | 11/2012 |
| GB | 1256866 A | 12/1971 |
| GB | 1274374 A | 5/1972 |
| GB | 2418861 A1 | 4/2006 |
| GB | 2422112 A | 7/2006 |
| GB | 2533399 A | 6/2016 |
| JP | 7275282 A2 | 10/1995 |
| JP | 9173369 A | 7/1997 |
| JP | 2010523274 A | 7/2010 |
| RU | 1522475 A1 | 7/1995 |
| RU | 2220685 C1 | 1/2004 |
| RU | 2332975 C2 | 9/2008 |
| WO | 9746265 A1 | 12/1997 |
| WO | 0038747 A2 | 7/2000 |
| WO | 0205735 A1 | 1/2002 |
| WO | 03026541 A1 | 4/2003 |
| WO | 04080358 A1 | 9/2004 |
| WO | 2007067111 A1 | 6/2007 |
| WO | 2008124715 A2 | 10/2008 |
| WO | 2013030581 A1 | 3/2013 |
| WO | 2013130564 A1 | 9/2013 |
| WO | 2014181338 A2 | 11/2014 |
| WO | 2014181339 A2 | 11/2014 |
| WO | WO-2016124203 A1 * | 8/2016 ............ A61F 5/443 |
| WO | 17044896 A1 | 3/2017 |
| WO | 2017067558 A1 | 4/2017 |
| WO | 17158340 A1 | 9/2017 |
| WO | 2017190752 A1 | 11/2017 |
| WO | 2018188705 A1 | 10/2018 |
| WO | 2018188706 A1 | 10/2018 |
| WO | 2018188707 A1 | 10/2018 |

* cited by examiner

ADHESIVE WAFER WITH A NEUTRALIZER MATRIX

The invention relates to an adhesive wafer for an ostomy appliance.

SUMMARY OF THE INVENTION

One aspect of the disclosure provides an adhesive wafer in accordance with the appended claim 1.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

DETAILED DESCRIPTION

Figure 1:
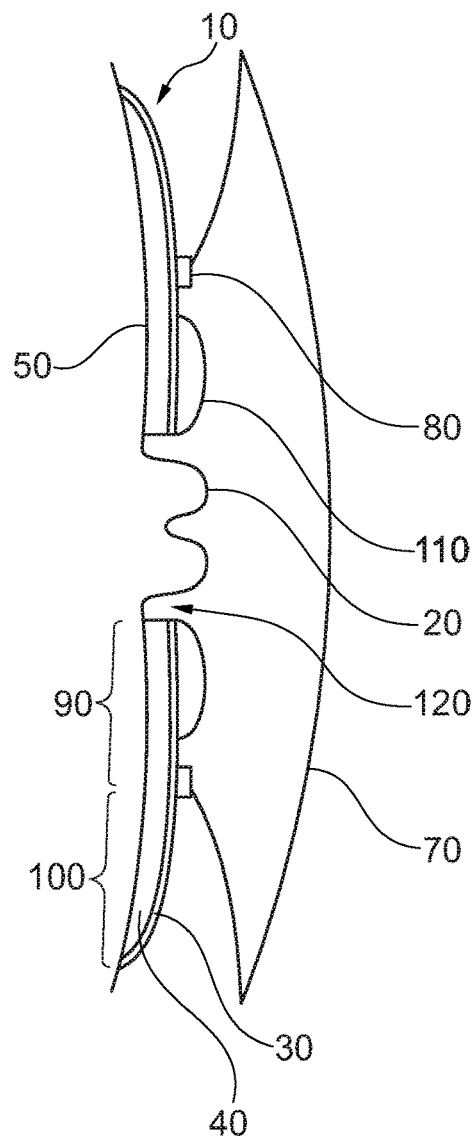
FIG. 1 illustrates a schematic cross-section view of one embodiment of a wafer.

In the following, whenever referring to the proximal side of a device or part of a device, the referral is to the skin-facing side, when the wafer or ostomy appliance is worn by a user. Likewise, whenever referring to the distal side of a device or part of a device, the referral is to the side facing away from the skin, when the wafer or ostomy appliance is worn by a user. In other words, the proximal side is the side closest to the user, when the wafer is fitted on a user and the distal side is the opposite side—the side furthest away from the user during use.

An axial direction is defined as the direction of the stoma, when the appliance is worn by a user. Thus, the axial direction is substantially perpendicular to a skin surface of a user, such as an abdominal skin surface. A radial direction is defined as transverse to the axial direction.

Prior to application to the skin a protective release liner may cover the skin contacting side of a pressure sensitive adhesive layer, in order to ensure that the properties of the adhesive are preserved and that the adhesive surface is not laid open until just before use. The release liner may suitably be a siliconised or fluorinated release liner, such as a siliconised or fluorinated craft paper, polyethylene, polypropylene or polyethylene terephthalate film. Suitably, the release liner is a siliconised polyethylene film, such as medium density polyethylene from the company Huhtamaki.

In the following, the words 'ostomy' and 'stoma' are used interchangeably without any intention to have different meanings.

By output is herein meant the effluent from a stoma, being faeces and/or urine in a more or less viscous form or mucins secreted from the epithelial layer of the alimentary canal. In the case of a colostomy, the output may be quite solid, whereas an ileostomy may produce more liquid output. The output may contain digestive fluids with enzymes and other components that may be aggressive to the skin and thus may cause maceration and contact dermatitis of the skin if brought into contact with it as well as the output may comprise components that may attack and degrade the adhesive.

Embodiments provide an ostomy appliance comprising an adhesive wafer for an ostomy device, the wafer comprising a proximal (skin-facing) adhesive layer, a backing layer on the distal (non-skin-facing) side of the adhesive layer, and a hole for accommodating a stoma, a connection zone, for attaching a collecting bag, circumferending the hole in a radial distance, and a release layer configured to releasing a neutralizer on the distal side of the backing layer, the release layer is located on at least a central portion of the backing layer, the central portion being defined as the area extending radially from the edge of the hole to a connection zone, wherein the neutralizer is selected from the group consisting of: AMBERLITE IRA 958 chloride, DEUREX Pure, DIANION WA30, Cholestyramine, DIANION HP 20, DIANION HP 2MG, TOYO PEARL, Kaolin, Calcium acetate, Calcium carbonate, Zinc sulphate, Zinc oxide, Strontium chloride, Lima bean inhibitor, Ovomucoids, pancreatic inhibitor/Kunitz inhibitor, Aprotinin, papaya Kunitz-type trypsin inhibitor, soybean trypsin inhibitor, potato trypsin inhibitor, barley trypsin inhibitor and squash trypsin inhibitor.

The wafer may be a part of an ostomy appliance comprising an adhesive wafer and a collecting bag. The collecting bag may be detachably or permanently attached to the wafer along a connection zone circumferencing the hole in a radial distance and having an inlet corresponding with the hole in the wafer.

The wafer comprises a central portion, defined as the area extending radially from the edge of the hole to the connection zone and a peripheral portion, defined as the area extending radially from the connection zone to the outer edge of the wafer.

When an ostomy wafer is applied to the skin surrounding a stoma, the adhesive provides a tight fit to the skin, in order to avoid the output from leaking under the wafer and damaging the skin and degrading the adhesive. Any output creeping under the wafer is to be avoided as much as possible as it may lead to maceration of the skin and degradation of the adhesive, resulting in leakage, unintended detachment of the wafer and discomfort to the user. Having a neutralizer matrix on the distal side of the backing layer, the output will be neutralized before attacking the skin and/or the adhesive.

When fitting a hole of an ostomy wafer to the area around a stoma, there will be a gap between the edge of the hole in the adhesive plate and the stoma. The stoma needs room to work due to inter alia peristaltic movements of the intestine; it enlarges when delivering output and shortens when not. In this gap, also called the peristomal gap, output from the stoma may enter and over time degrade the adhesive layer as well as cause skin maceration. By providing a release layer configured to releasing a neutralizer at least at a central portion of the distal surface of the backing layer, the release layer may easily get in contact with the output and release neutralizer to the peristomal gap, and the skin and the adhesive at the peristomal gap will be protected. Some of the neutralizer will be flushed into the bag by the output, but most of the neutralizer will flow into the peristomal gap and interact with the output to neutralize its harmful components.

The output from the stoma may flow substantially continuously or it may enter the bag in bursts, e.g. depending on the type of stoma. If the user of the bag is in an upright position, continuous output may flow downwards due to gravity and primarily wet the part of the central portion of the wafer being below the stoma. However, the output may also creep upwards to wet the part of the central portion above the stoma. When coming in bursts, and inside a bag and with the distal wall of the bag close to the stoma, the output may spread all over the central portion of the backing layer, including also the area above the stoma. A user wearing a bag with clothing potentially pushing the bag wall towards the stoma, the output may for a period of time be trapped in and fill the volume defined by the wafer, the distal wall and the connection zone. Thus, the output may not immediately follow gravity but will also wet the area of the bag being above the stoma receiving hole and also the entire peristomal gap.

In embodiments, the release layer is located on at least a part of the central portion of the backing layer and the release layer may extend further radially outwards to cover a part of the inner wall of the bag.

In embodiments, the release layer is provided on the distal side of the adhesive layer, in direct contact with the proximal surface of the adhesive layer. The adhesive layer being in direct contact with the release layer—without a backing layer in between, enables attachment of the release layer to the wafer. By having the release layer in direct contact with the adhesive layer, any material compatibility problems may be avoided.

In embodiments, a portion of the release layer is in direct contact with the distal surface of the adhesive layer and another part of proximal surface of the release layer is overlying a part of the distal surface of the backing layer. In embodiments, an entire proximal surface of the release layer is in direct contact with the distal surface of the adhesive layer.

In embodiments, the release layer is at least located next to the hole. This enables the neutralizer to easily enter the peristomal gap when released from the release layer. By next to the hole is meant being extending radially inwards to define at least a part of the rim of the hole. In embodiments, the release layer is located on at least a part of the central portion of the backing layer.

In embodiments, the release layer comprises a matrix with a neutralizer incorporated therein. The matrix serves as a carrier of the neutralizer and is capable of releasing the neutralizer.

By neutralizer is herein meant a neutralizing substance capable of neutralizing or at least minimizing the level of skin- or adhesive-aggressiveness of the output.

In embodiments, the neutralizer comprises a clay, such as organophilic clay, for example bentonite or synthetic clay such as LAPONITE. Examples of such clays are disclosed in EP 1 140 009. In embodiments, the neutralizer may be potato-derived inhibitors or protease inhibitors. Examples of potato-derived inhibitors such as potato protein are disclosed in EP 1 736 136.

The neutralizer is selected from the group consisting of: AMBERLITE IRA 958 chloride, DEUREX Pure, DIANION WA30, Cholestyramine, DIANION HP 20, DIANION HP 2MG, TOYO PEARL, Kaolin, Calcium acetate, Calcium carbonate, Zinc sulphate, Zinc oxide, Strontium chloride, Lima bean inhibitor, Ovomucoids, pancreatic inhibitor/ Kunitz inhibitor, Aprotinin, papaya Kunitz-type trypsin inhibitor, soybean trypsin inhibitor, potato trypsin inhibitor, barley trypsin inhibitor and squash trypsin inhibitor.

The Lima bean inhibitor is a Lima bean trypsin inhibitor which inhibits bovine as well as human trypsin and plasmin, acts upon both trypsin and chymotrypsin by forming equimolar complexes, Ovomucoids are a protease inhibitors of avian egg white. Egg whites comprises several protease inhibitors. Pancreatic inhibitor/Kunitz inhibitor, Aprotinin (lung tissue), papaya Kunitz-type trypsin inhibitor are trypsin inhibitors. Soybean trypsin inhibitor inhibits trypsin mole-for-mole and to a lesser extent chymotrypsin.

Other suitable neutralizers are AMBERLITE IRA 958 chloride, DEUREX Pure, DIANION WA30, Cholestyramine, DIANION HP 20, DIANION HP 2MG, TOYO PEARL, Kaolin, Calcium acetate, Calcium carbonate, Zinc sulphate, Zinc oxide, and Strontium chloride.

In embodiments, the neutralizer is a plant based trypsin inhibitor isolated from plants selected from the group consisting of: Kunitz's Soybean, erythrina seed, winged bean, prosopis juliflora seed, Philippine acacia (Acacia confuse) seed, Albizzia jubibrissin, Acacia elata seed, Enterolobium contortisiliquum seed, Bauhinia seed, Delonix regia seed, Crotalaria paulina seeds, velvet bean (*Mucuna pruriens*), *Dimorphandra mollis* seeds, Brazillian tree *Copaifera langsdorffii* seed and soybean proteinase inhibitor (Bowman-Birk) family.

In embodiments, the neutralizer is a plant based protein isolated from plants selected from the group of consisting of: lima bean, garden beans, adzuki beans, mung beans, ground nuts, chickpeas, pigeon pea (cajanus cajan), peas (*Pisum sativum*), cowpeas (*Vigna unguiculate*), winter peas (*Pisum Arvenue*), white sword bean (*Canavalia gladiate*), wheat germ, rice, lentils, barley, soy flour, soybean, peanuts (*Arachis hypogaea*), red kidney beans (*Phaseolus vulgaris*), Brazilian pink bean (*P. vulgaris*), bush bean (*Phaseolus vulgaris*), horsegram (*Dolichos biflorus*), fenugreek (*Trigonella* foenum graecum) seeds, Alfalfa (Lucerne, *Medicago sativa*), Torresea *cearensis*, Leguminosae seeds, *Dioclea glabra* seeds, Jobs tears (*Coix* lachrymal), wheat, barley, papaya (*Carica papaya*) and Potato I and II inhibitor family.

In embodiments, the neutralizer is a trypsin inhibitor. In embodiments, the neutralizer is a chymotrypsin inhibitor. In embodiments, the neutralizer is selected from the group consisting of: Polypeptide chymotrypsin inhibitor I and II, Trypsin-chymotrypsin inhibitor from potato tuber, Sweet potato (*Iponoea batatas*) trypsin inhibitor, Protease inhibitor from potato juice of cv. Elkana and Potato tuber inhibitor (*Solanum tuberosum*).

In embodiments, the neutralizer is selected from the group of trypsin inhibitors isolated from the squash family (Cucurbitaceae) consisting of: sqaush seeds, Winter squash (*Cucurbita maxima*), Melon seed (*Cucumis melo*), Cucumber seed, fig leaf gourd seeds (*Cucurbita ficifolia*), Bitter gourd seed (*Momordica charantia*), Ridged gourd (*Luffa acutangula*) seed, Ridged gourd (*Luffa acutangular*) seed, Wild cucumber seed (*Echinocystis lobate*), spiny bitter seed (*Momordica cochinchinsis*) and Squash spiny bitter seed.

In embodiments, the neutralizer is selected from the group of trypsin inhibitors isolated from the group consisting of: cereal grains, barley, barley trypsin inhibitor family, rye, maize, Amylase-trypsin inhibitor from Ragi seed, wheat germ trypsin inhibitor, buckwheat seeds, amaranth (*Amatanthus caudatus*) seeds, Amaranth hypochondricus seeds and Mustard trypsin inhibitor from white mustard (*Sinapis alba*), In embodiments, the neutralizer is selected from the group of trypsin inhibitors consisting of: Rapeseed trypsin inhibitor (RTI), Bauhinia seeds trypsin inhibitor, Kohlrabi trypsin inhibitor, Cabbage seed protease inhibitor, *C. fistula* seed protease inhibitor and *Cassia fistula* seed trypsin inhibitor.

In embodiments, the neutralizer is selected from the group of trypsin inhibitors isolated from the group consisting of: Peanuts, groundnut, pigeon pea, red gram, Jack bean, sword bean, partridge pea, Chickpea, Bengal gram, Garbanzo, butterfly pea, Cluster bean, Horse gram, hyacinth bean, fiels bean, Hakubenzu bean, Double bean, soybean, sweet pea, Chickling vetch, lentil, Lupine, Florida velvet bean, Moth bean, Adzuki bean, Mung bean, green gram, Scarlet runner bean, Lima bean, butter bean, Black gram, Navy bean, kidney bean, pinto bean, French bean, white bean, wax bean, harticot bean, garden bean, Field bean, winged bean, Gao bean, velvet bean, Broas bean, *faba* bean, Cowpea, black-eyed pea, Southern pea, serido pea, Bambara bean.

In embodiments, the matrix is a composition in which the neutralizer is incorporated. The neutralizer may be dissolved in the matrix or it may be dispersed as particles in the matrix.

In embodiments, the release layer may be in the form of coated neutralizer particles.

In embodiments, the matrix of the release layer is designed to release neutralizer when the release layer is exposed to certain conditions. Such conditions may for example be in the presence of output from the stoma or in the presence of moisture.

Inside a collecting bag, the humidity will quickly reach about 100% humidity, so the presence of moisture is substantial. In embodiments where the release layer is sensitive to moisture, the release of neutralizer from the release layer may initiate shortly after applying the wafer, due to the high humidity in the bag.

In embodiments, the matrix is in the form of a gel, foam, film layer, paper or a coating.

Such coating may for example be solid or powder coating. In embodiments, the matrix and the neutralizer form a colloidal solution such as a sol.

In embodiments, a matrix in the form of a water-soluble film such as a polyvinyl alcohol film, for example a Monosol 7031 film.

In embodiments, the matrix is soluble in water or a component of the output. It may be slowly soluble, by slowly is herein meant that the matrix layer will not be washed away instantly, but will slowly dissolve and provide a steady release of neutralizer over time, for example during wear time of the wafer. In embodiments, the matrix is swelling during absorption of moisture.

In embodiments, the matrix may absorb moisture and turn into a gel like material when wetted. The matrix may be delivered in dry form and swell into a gel when brought into contact with moisture. In embodiments, the matrix is delivered as a gel. In embodiments, the gel may be slowly soluble in water or in a component of the output or it may be insoluble but able to release the neutralizer when exposed to stomal output or moisture. In embodiments, the matrix is a material capable of forming a gel when wetted or it may be in the form of a gel. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine.

In embodiments, the matrix comprises water-soluble or water-swellable polysaccharides and/or hydrocolloids. The polysaccharides or hydrocolloids may dissolve or hydrate when exposed to moisture from the output, thereby releasing neutralizer.

In embodiments, the matrix comprises protein. In embodiments, the matrix comprises gelatine.

In embodiments, the matrix is substantially non-adhesive. By non-adhesive is meant that it is not adhesive, though it may, under certain conditions, become slightly sticky.

A non-adhesive matrix will be less prone to sticking to the distal wall of the bag and cause problems in that way.

Embodiments provide an ostomy appliance comprising a collecting bag and an adhesive wafer, the wafer comprising a proximal (skin-facing) adhesive layer, a backing layer on the distal (non-skin-facing) side of the adhesive layer, and a hole for accommodating a stoma, a connection zone, for attaching a collecting bag, circumferending the hole in a radial distance, and a release layer configured to releasing a neutralizer on the distal side of the backing layer, the release layer is located on at least a central portion of the backing layer, the central portion being defined as the area extending radially from the edge of the hole to a connection zone, wherein the neutralizer is selected from the group consisting of: AMBERLITE IRA 958 chloride, DEUREX Pure, DIANION WA30, Cholestyramine, DIANION HP 20, DIANION HP 2MG, TOYO PEARL, Kaolin (from adhesive lab), Calcium acetate, Calcium carbonate, Zinc sulfate, Zinc oxide, Strontium chloride, Lima bean inhibitor, Ovomucoids, pancreatic inhibitor/Kunitz inhibitor, Aprotinin, papaya Kunitz-type trypsin inhibitor, soybean trypsin inhibitor, potato trypsin inhibitor, barley trypsin inhibitor and squash trypsin inhibitor.

The collecting bag usually comprises a front wall on the distal side and a rear wall on the proximal side. The walls may be made of gas- and liquid impermeable foil-material (for example of polyethylene (PE), polyvinyl-chloride (PVC) or ethylene-vinyl-acetate (EVA)) that is welded around the edges or the rim, so as to form a pouch defining a waste collection chamber. The bag may be welded only partly around the rim so that an opening for emptying the bag is provided at the bottom of the bag. In that case, the bag may be provided with means for closing that opening. The waste inlet opening is provided in the rear wall and placed in the upper part of the collecting bag, so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part.

In embodiments, the backing layer is gas and water impermeable. In embodiments, the wafer comprises an adhesive layer proximal to the skin, a backing layer on the distal surface of the adhesive layer and a release layer on at least a part of the distal surface of the backing layer. Thus, the release layer is furthest away from the skin and is located on the central portion of the backing layer defining a part of an inside surface of the collecting bag.

In embodiments, an ostomy appliance may be produced by providing an adhesive wafer, the wafer comprising a proximal adhesive layer, a backing layer on the distal side of the adhesive layer, and a hole for accommodating a stoma, attaching the rear wall of a collecting bag along a connection zone on the backing layer, for example by welding, providing a release layer on the distal side of the central portion of the backing layer and optionally extending further radially to cover at least a part of the rear wall, and then superimposing the distal wall over the rear wall and welding the rear wall and the distal wall together along the rim to provide a closed bag.

Disclosed is a method of protecting the peristomal skin of a user, the method comprising the following steps: providing an ostomy appliance comprising a collecting bag and an adhesive wafer, the wafer comprising a proximal adhesive layer, a backing layer on the distal side of the adhesive layer, and a hole for accommodating a stoma, and a release layer configured to releasing a neutralizer on the distal side of the backing layer; optionally adapting the size of the hole to fit a stoma; and attaching the wafer to the skin around a stoma. The output from the stoma may distribute over the central portion of the wafer and into the peristomal gap between the hole and the stoma, thereby flushing over the release layer and releasing the neutralizer into the peristomal gap. The aggressive output from the stoma will be neutralized before or shortly after reaching direct skin contact at the peristomal gap and the skin will be less prone to irritation due to the contact with the output.

Embodiments, and features of the various exemplary embodiments described in this application, may be combined with each other ("mixed and matched"), unless specifically noted otherwise.

DETAILED DESCRIPTION OF THE DRAWING

In the following detailed description, reference is made to the accompanying drawings. The drawings form a part of this specification and illustrate exemplary embodiments for practicing the invention. Directional terminology, such as "top," "bottom," "front," "back," etc., is used with reference to the orientation of the figures being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Initially, it shall be noted that the figures are schematic illustrations intended only to address the principles and functions of the wafer according to the invention and are not to be considered limiting to the scope of the attached claims. Furthermore, the figures and particularly the individually illustrated elements are not necessarily to scale, neither individually nor in relation to each other.

In FIG. 1 is shown a cross-sectional view of an ostomy appliance. The appliance comprises an adhesive wafer 10 having a proximal layer of adhesive 40 facing the skin and for attaching the wafer to the skin 50 surrounding a stoma 20. A backing layer 30 covering the distal surface of the adhesive layer 40. A central hole 60 is provided for accommodating a stoma 20. The size of the hole 60 may be adapted by cutting to tailor fit the hole 60 to the stoma 20. The wafer is provided with a collecting bag 70, the bag being connected to the wafer along a connection zone 80 circumferencing the hole 60 in a radial distance. The bag 70 may be detachably connected to the wafer 10 in a way so that the bag 70 may be detached from the wafer 10 and exchanged, or the bag 70 may be inseparately connected to the wafer 10 for example by welding. The wafer 10 comprises a central portion, defined as the area extending radially from the hole 60 to the connection zone 80 and a peripheral portion 100, defined as the area extending radially from the connection zone 80 to the outer edge of the wafer 10. At least a part of the distal surface of the central portion 90 is provided with a release layer 110. The release layer 110 may be in the form of a disc essentially covering the entire central portion 90 of the distal surface or it may be primarily in the area of the distal surface being next to the hole 60. When cutting the hole 60, the release layer 110 may be cut too. When output from the stoma 20 is flowing from the stoma and over the release layer 110, it may release the neutralizer that enters into the peristomal gap 120 between the edge of the hole 60 and the stoma 20.

Figure 2:
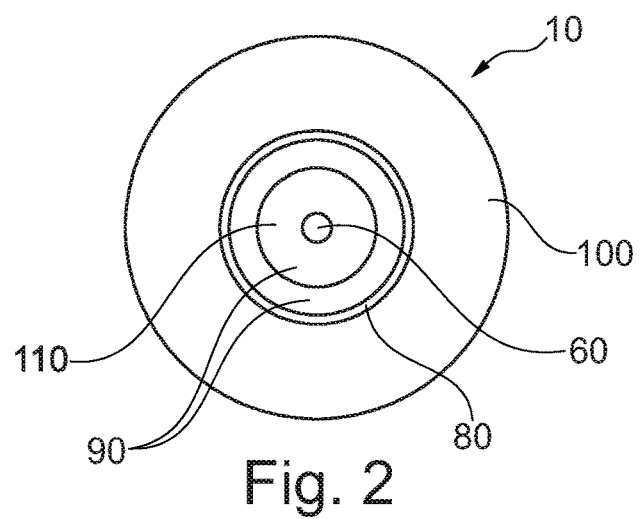
FIG. 2 illustrates a plan view of an embodiment of a wafer.

FIG. 2 shows an embodiment of an adhesive wafer 10 seen from the distal side, with a central portion 90 surrounding a hole 60 for accommodating a stoma 20, and a peripheral portion 100 circumferencing the central portion. Along the transition between the central portion 90 and the peripheral portion 100 is the connection zone 80. The connection zone 80 may be in the form of a coupling for attaching a collecting bag (not shown). On a part of the distal surface of the central portion 90, closest to the hole 60, is provided a release layer 110.

Example

An ostomy wafer (Sensura from Coloplast A/S) is provided. In a solution of PEG is suspended 1% particles of Protagold potato protein. The dispersion is placed onto the distal side of the central portion of the adhesive wafer and dried to form a 0.5 mm thick film layer.

Experimental

Distribution of Neutralizer (Flow Model)

A silicone cast of a stoma was made, and a hole was cut through it. One end of the stoma was attached to a syringe, which was used in order to control the flow through the stoma and creating an illusion of a flow of output from an intestine through the stoma.

The other end of the stoma was placed in a hole in a vertical plastic plate to simulate the stoma protruding through stomach wall.

Once the stoma model was set up, a Sensura wafer from Coloplast A/S, provided with a release layer on the distal surface of the central portion of the backing layer was placed on the peristomal skin, with the release layer of the wafer being located on the surface facing away from the skin. The release layer comprised a matrix composition in the form of PEG (polyethylene glycol) and the neutralizer was represented by particles of amaranth (red colour dye) distributed homogenously in the matrix composition in a concentration of approximately 1%. The release layer was disposed on the central portion of the backing layer of the wafer in a thickness of approximately 0.5-1 mm.

Stomal output was represented by a viscous aqueous solution of carboxy methyl cellulose (CMC). When the output was pushed through the syringe, it flowed through the stoma, and down over the adhesive wafer and the release layer. When the flow was slowed down, it was possible to visually verify that the red colour also moved against the flow direction and towards the center of the stoma, even despite of gravity. This indicates that at least a part of the neutralizer will flow from the release layer on the adhesive wafer to enter into the peristomal gap between the wafer and the stoma, and will thereby be able to protect the skin in the peristomal area by neutralizing the output.

Figure 3A:
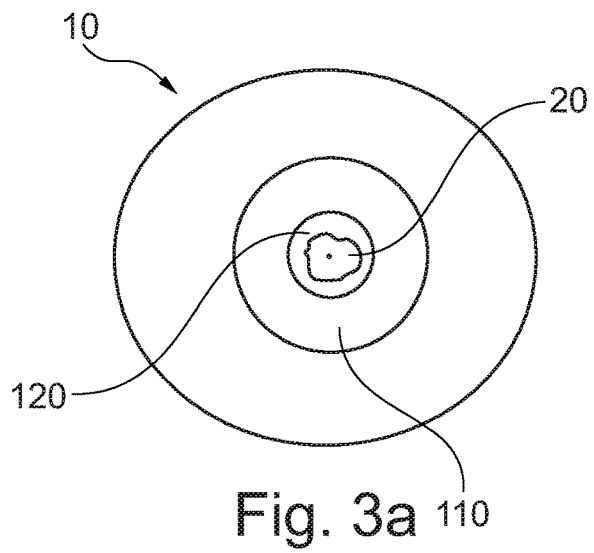
FIG. 3a-3c illustrate the flow of red dye in an embodiment of a wafer.
Figure 3B:
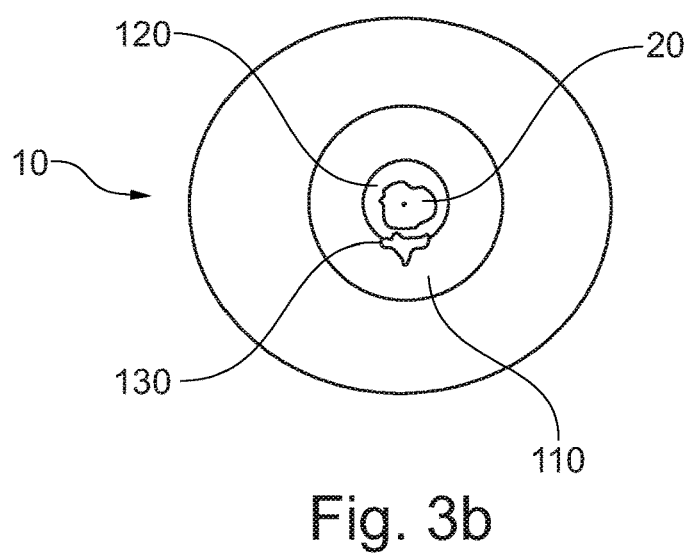
Figure 3C:
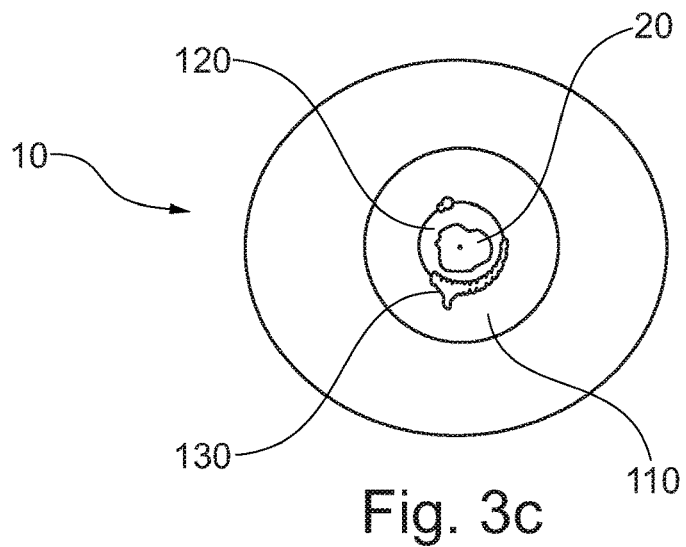
Figure 3D:
FIG. 3d is a photo of a stoma flow model.

The phenomenon is illustrated in FIG. 3a-3c showing how the red dye distributes when the output is passed through the stoma. The wafer 10 was provided with a release layer 110 in which the content of neutralizer had been substituted with red dye as described above. FIG. 3a shows the wafer before output is introduced. In FIG. 3b, the output flows from the stoma 20 to wet the release layer 110, thereby releasing the red dye 130. As can be seen from the Figure, some of the dye passed downwards, due to gravity, whereas some of it flowed in the opposite direction, towards the stoma 20 and into the peristomal gap 120 between the stoma 20 and the wafer 10. Output may often come in bursts rather than a constant flow. Between the bursts, the neutralizer (red dye) flows into the peristomal gap 120. However, during a continuous flow of output from the stoma, retrograde flow is also seen. In FIG. 3c is shown how the neutralizer (red dye) 130 was released after a burst of output; the release was all the way round the stoma 20 and not only below the stoma 20. In FIG. 3d is shown a photo of the stoma model, with output flowing from the stoma and over the release layer.

Release of Neutralizer from the Release Layer

A composition was prepared as shown in Table 1:

TABLE 1

|  | Sample w/w |
| --- | --- |
| PEG | 41.7 |
| Laponite | 20.8 |
| Starch | 37.5 |

For testing the release of LAPONITE from the sample, 2 g of sample was placed in basket, 60 ml of PBS buffer (phosphate buffered saline) placed in cup and the basket was placed in the cup. The buffer was stirred by magnetic stirrer at 100 rpm and temperature was kept at 37° C. Measurements were in triplicates. The measuring method was yielding a 20% uncertainty. The buffer samples were analyzed for their content of LAPONITE using Atomic Absorption Spectroscopy AAS. After 2 hours, 79% of the LAPONITE was released to the buffer. Hence, the composition is capable of releasing the neutralizer into the buffer.

An Explorative Study Investigating Human Skin Reaction to Output

In a clinical setting the effect of feces on human skin was investigated using 22 subjects having an ileostomy. At the beginning of the study all subjects had their ostomy product removed from the skin leaving the skin to acclimatize for 30 min. This was followed by measuring the transepidermal water loss (TEWL) at the beginning of the study to obtain the start value. The TEWL measurement describes the status of the skin barrier function and can be used to evaluate a damage to the skin.

All subjects had an ostomy product applied where part of the product was removed to make space for three small bags. These bags were in 12 of the subjects filled with respectively a buffer solution, the subject's own feces and a simulated feces solution containing trypsin and chymotrypsin. The bags were in the remaining 10 subjects filled with the same solutions but mixed with 5% of LAPONITE RD.

All small bags were incubated on the peristomal skin for 6 hours before the bags were removed. The skin areas were cleaned and left to acclimatize for 30 min before the TEWL was measured again in the respective skin areas.

Figure 4:
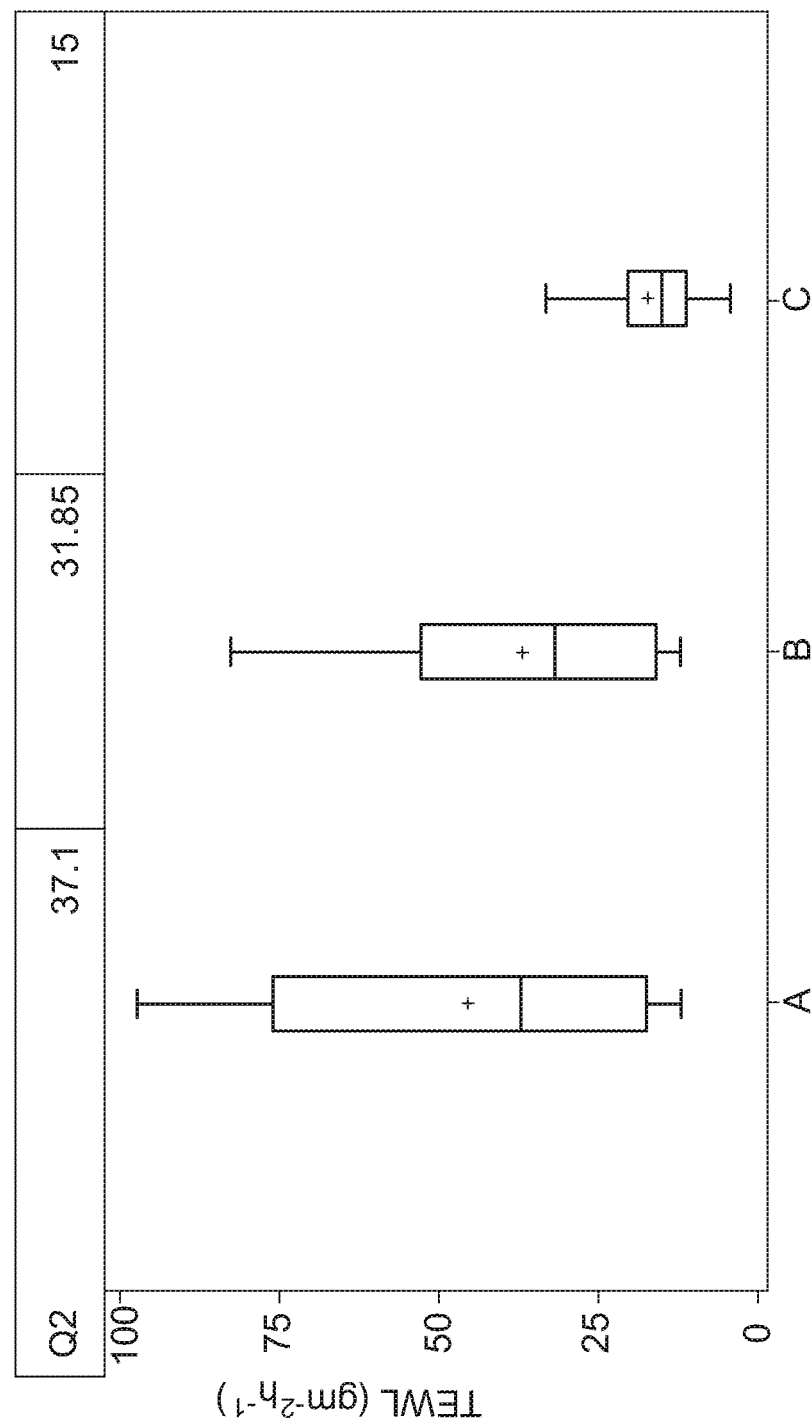
FIGS. 4 and 5 show boxplots and statistical analysis of TEWL (Trans Epidermal Water Loss).

In FIG. 4 is shown a boxplot and a statistical analysis of TEWL on the peristomal area of the samples without LAPONITE RD (neutralizer).

The median TEWL results showed, as seen in FIG. 4, a significant higher value for skin incubated with real feces (A in the Figure) (P<0.001) as well as the simulated feces (B in the Figure) (P=0.001) compared to the buffer incubated skin (C in the Figure). This means that both real feces and simulated feces results in damage to the barrier of the skin. There was no difference between the damage seen with real feces or simulated feces (P=0.415).

Figure 5:
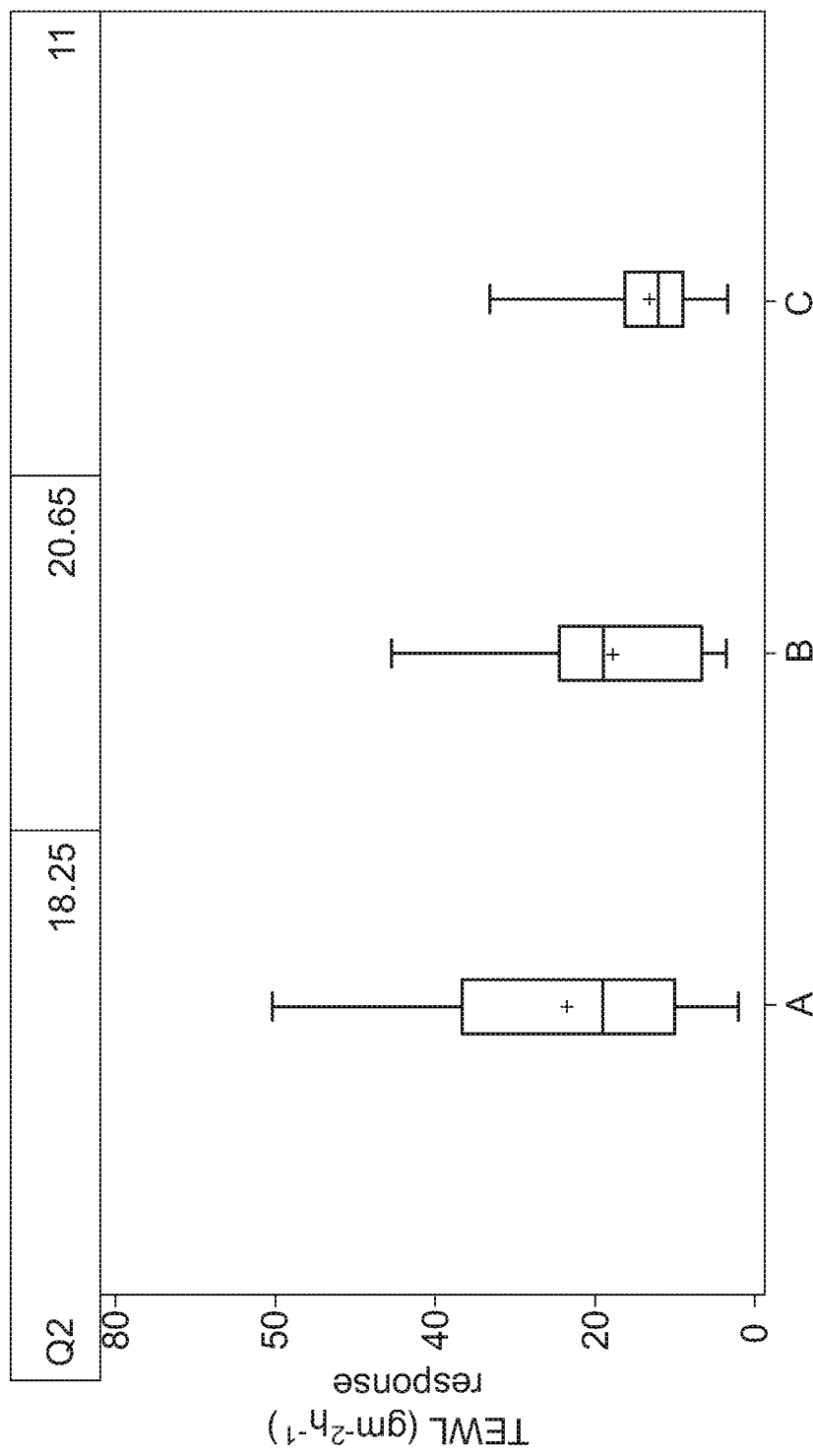

In FIG. 5 is shown a boxplot and statistical analysis of TEWL on the peristomal area of the samples containing LAPONITE RD (A', B' and C' in the Figure).

When the subject's own feces, simulated feces with enzymes or buffer were mixed with LAPONITE RD there were no significant difference between own feces (P=0.112) or simulated feces (P=0.175) compared to buffer with the LAPONITE RD. There was no significant difference between own feces or simulated output when LAPONITE RD were mixed into the solutions.

In conclusion, we saw a significant increase, compared to incubating with buffer, in the trans epidermal water loss (TEWL) from skin when the subject's own feces or simulated feces were incubated on the peristomal skin for 6 hours meaning a damage to the barrier of the skin.

Mixing the LAPONITE RD into the same solutions/suspensions did not influence the TEWL and thereby did not affect the barrier of the skin. LAPONITE RD mixed into feces or simulated feces neutralizes the damaging effect of these suspensions protected the skin from being damaged.

The invention claimed is:

1. An adhesive wafer for an ostomy device, the adhesive wafer comprising:
    a backing layer;
    an adhesive layer deposited on a proximal side of the backing layer, the adhesive layer attachable to skin around a stoma of a user;
    a hole formed through the adhesive wafer, with an edge of the hole defining an inner rim of the adhesive wafer; and
    a release layer deposited on a distal side of the backing layer, where a first portion of the release layer is uncovered for exposure to stomal output from the stoma;
    wherein the first portion of the release layer, when exposed to the stomal output, is adapted to release a neutralizer into a peristomal gap between the inner rim of the adhesive wafer and the stoma of the user;
    wherein the neutralizer neutralizes and reduces aggressiveness of the stomal output to the adhesive layer, and the neutralizer is selected from the group consisting of cholestyramine, kaolin, calcium acetate, calcium carbonate, zinc sulfate, zinc oxide, strontium chloride, lima bean inhibitor, ovomucoids, pancreatic inhibitor, aprotinin, papaya trypsin inhibitor, soybean trypsin inhibitor, potato trypsin inhibitor, barley trypsin inhibitor, and squash trypsin inhibitor.

2. The adhesive wafer of claim 1, wherein the first portion of the release layer is located at the inner rim of the adhesive wafer.

3. The adhesive wafer of claim 1, wherein a proximal portion of the release layer is in contact with a distal side of the adhesive layer.

4. The adhesive wafer of claim 1, further comprising:
    a connection zone connected to a distal side of the backing layer, with the connection zone surrounding the hole and adapted to couple a collecting bag to the adhesive wafer.

5. The adhesive wafer of claim 4, wherein the release layer is deposited on at least a portion of an area between the inner rim and the connection zone.

6. The adhesive wafer of claim 1, wherein the neutralizer is incorporated in a matrix.

7. The adhesive wafer of claim 6, wherein the matrix is soluble in water.

8. The adhesive wafer of claim 6, wherein the matrix is a gel.

9. The adhesive wafer of claim 6, wherein the matrix is a foam.

10. The adhesive wafer of claim 6, wherein the matrix comprises a polysaccharide.

11. The adhesive wafer of claim 1, wherein the neutralizer is configured to be released in presence of moisture.

12. The adhesive wafer of claim 1, wherein the squash trypsin inhibitor is isolated from the squash family (cucurbitaceae) selected from the group consisting of: squash seeds, winter squash (*Cucurbita maxima*), melon seed (*Cucumis melo*), cucumber seed, fig leaf gourd seeds (*Cucurbita ficifolia*), bitter gourd seed (*Momordica charantia*), ridged gourd (*Luffa acutangula*) seed, ridged gourd (*Luffa acutangular*) seed, wild cucumber seed (*Echinocystis lobate*), spiny bitter seed (*Momordica cochinchinsis*), and squash spiny bitter seed.

13. The adhesive wafer of claim 1, further comprising:
a waste collection bag permanently connected to the adhesive wafer, where the release layer is located within the waste collecting bag.

14. The adhesive wafer of claim 1, wherein the potato trypsin inhibitor is derived from one of a potato tuber, sweet potato (*Iponoea batatas*) trypsin inhibitor, protease inhibitor from potato juice of cv. elkana, and potato tuber inhibitor (*Solanum tuberosum*).

15. The adhesive wafer of claim 1, wherein a first portion of the release layer is in contact with a distal side of the adhesive layer and a second portion of the release layer overlaps and is in contact with a distal side of the backing layer.

16. The adhesive wafer of claim 1, wherein the release layer is an annular release layer disposed around an entire circumference of the hole formed through the adhesive wafer.

17. The adhesive wafer of claim 1, wherein the release layer covers a partial length of the backing layer within the central portion of the adhesive wafer.

18. The adhesive wafer of claim 1, wherein the release layer is positioned within only a central portion of the adhesive wafer.

19. The adhesive wafer of claim 1, wherein the neutralizer flows from the peristomal gap toward the stoma.

* * * * *